US008845590B2

(12) United States Patent
Ash

(10) Patent No.: US 8,845,590 B2
(45) Date of Patent: Sep. 30, 2014

(54) CATHETER WITH DISTAL DIFFUSER

(75) Inventor: Stephen R. Ash, Lafayette, IN (US)

(73) Assignee: Merit Medical Systems, Inc., South Jordan, UT (US)

(*) Notice: Subject to any disclaimer, the term of this patent is extended or adjusted under 35 U.S.C. 154(b) by 199 days.

(21) Appl. No.: 13/461,452

(22) Filed: May 1, 2012

(65) Prior Publication Data
US 2013/0296770 A1 Nov. 7, 2013

(51) Int. Cl.
A61M 5/32 (2006.01)
A61M 25/18 (2006.01)
A61M 31/00 (2006.01)

(52) U.S. Cl.
USPC .......... 604/175; 604/533; 604/93.01

(58) Field of Classification Search
USPC .............. 604/30, 43, 175, 257, 277
See application file for complete search history.

(56) References Cited

U.S. PATENT DOCUMENTS

| 4,368,737 | A | * | 1/1983 | Ash | .................. 604/175 |
| 4,392,855 | A | | 7/1983 | Oreopoulos et al. | |
| 4,437,856 | A | | 3/1984 | Valli | |
| 4,559,033 | A | | 12/1985 | Stephen et al. | |
| 5,254,084 | A | | 10/1993 | Geary | |
| 6,231,544 | B1 | * | 5/2001 | Tsugita et al. | ............... 604/104 |
| 6,293,958 | B1 | | 9/2001 | Berry et al. | |
| 2009/0292272 | A1 | | 11/2009 | McKinnon | |

FOREIGN PATENT DOCUMENTS

WO WO2010/149168 12/2010
WO WO2012/040311 3/2012

OTHER PUBLICATIONS

International Search Report and Written Opinion dated Aug. 9, 2013 for PCT/US2013/038629.

* cited by examiner

Primary Examiner — Aarti B Berdichevsky
Assistant Examiner — Tien Tran
(74) Attorney, Agent, or Firm — Stoel Rives LLP

(57) ABSTRACT

A catheter configured with an elongate tube and a diffuser is disclosed. The diffuser may be configured to facilitate high flow rates through the catheter and to resist blockage of openings disposed within the body. Further, the catheter may be comprised of flexible materials to facilitate delivery into and removal from the body. In some embodiments the diffuser may be generally disc shaped.

17 Claims, 7 Drawing Sheets

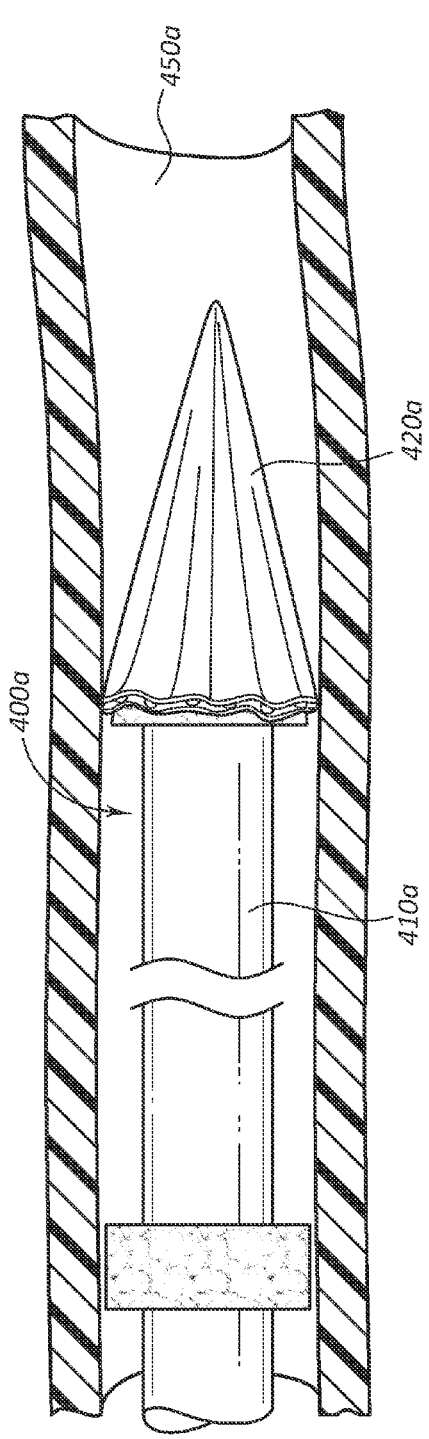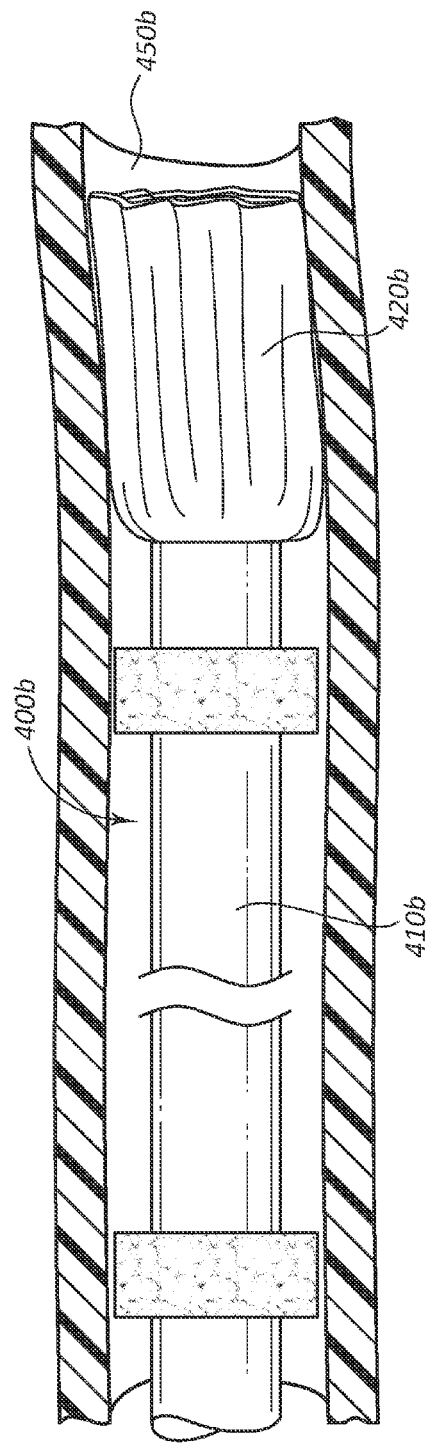
FIG. 9A
FIG. 9B

CATHETER WITH DISTAL DIFFUSER

TECHNICAL FIELD

The present disclosure relates generally to medical devices. More specifically, the present disclosure relates to catheters, including catheters comprising distally disposed diffuser portions. In some embodiments, the diffuser portion may be flexible, including embodiments wherein the diffuser is configured to be disposable in a radially constrained delivery configuration and a radially expanded deployed configuration.

BRIEF DESCRIPTION OF THE DRAWINGS

The embodiments disclosed herein will become more fully apparent from the following description and appended claims, taken in conjunction with the accompanying drawings. These drawings depict only typical embodiments, which will be described with additional specificity and detail through use of the accompanying drawings in which:

FIG. 9A is a side view of a catheter being deployed within a delivery lumen.

FIG. 9B is a side view of a catheter being retrieved within a lumen.

DETAILED DESCRIPTION

Catheters may be configured to allow fluid flow across body structures, including facilitating flow in and out of the body. In some instances, a catheter may comprise an elongate tube with a diffuser coupled to the distal end of the tube. The diffuser may be configured to direct flow in or out of the distal end of the tube, and/or to interact with the body. For instance, the diffuser may be configured to limit the extent to which bodily structures, such as the omentum, reduce flow through the catheter.

In some embodiments, a diffuser may be configured in a general disc shape, which may be oriented perpendicular to the longitudinal axis of the catheter lumen. A disc diffuser may be configured to direct flow in and out of the catheter as well as to resist blockage of the flow by the omentum or other bodily tissues. Further, a disc diffuser may comprise flexible materials which allow the disc to be constrained in a low-profile configuration, such as rolled around the elongate portion of the catheter. Such flexible discs may thus be inserted into the body through a sheath or other lumen, with the disc radially expanding from the rolled configuration when the diffuser is deployed.

It will be readily understood that the components of the embodiments as generally described and illustrated in the Figures herein could be arranged and designed in a wide variety of different configurations. Thus, the following more detailed description of various embodiments, as represented in the Figures, is not intended to limit the scope of the disclosure, but is merely representative of various embodiments. While the various aspects of the embodiments are presented in drawings, the drawings are not necessarily drawn to scale unless indicated.

The phrases "connected to," "coupled to," and "in communication with" refer to any form of interaction between two or more entities, including mechanical, electrical, magnetic, electromagnetic, fluid, and thermal interaction. Two components may be coupled to each other even though they are not in direct contact with each other. For example, two components may be coupled to each other through an intermediate component.

The directional terms "proximal" and "distal" are used herein to refer to opposite locations on a medical device. The proximal end of a device is defined as the end closest to the practitioner when the device is in use. The distal end is the end opposite the proximal end, along the longitudinal direction of the device, or the end furthest from the practitioner. It is understood that, as used in the art, these terms may have different meanings once a device is deployed (i.e., the "proximal" end may refer to the end closest to the head or heart of the patient depending on the application). For consistency, as used herein, the ends labeled "proximal" and "distal" prior to deployment remain the same regardless of whether the device is deployed.

Figure 1:
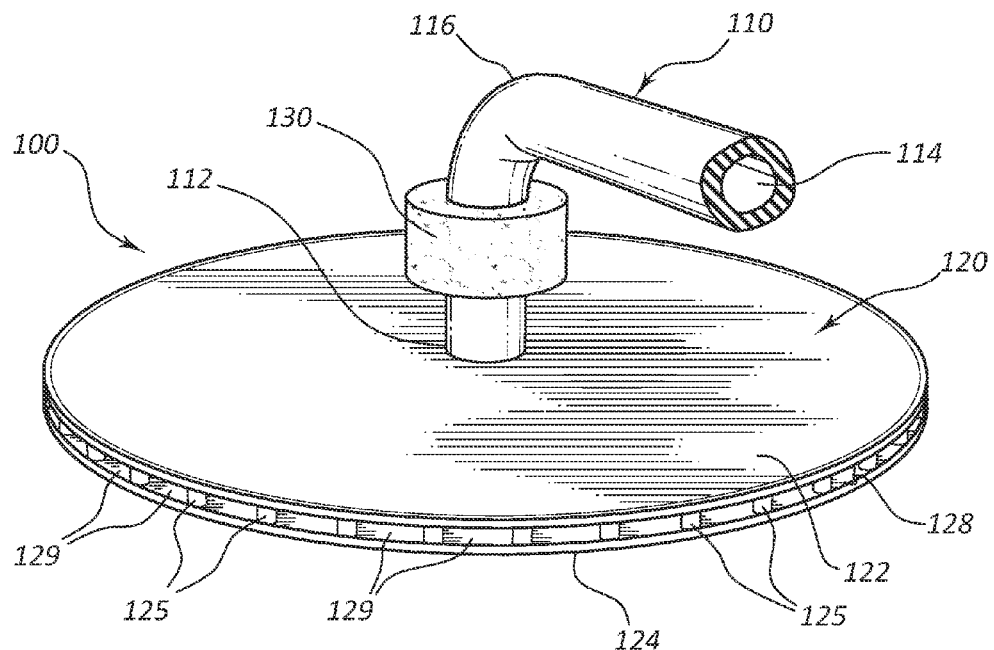
FIG. 1 is a partially cut-away perspective view of a catheter.

FIG. 1 is a perspective view of a catheter 100. The catheter 100 of the illustrated embodiment comprises an elongate tube 110 coupled to a diffuser 120. The elongate tube 110 extends between a proximal end (not shown) and a distal end 112. In the illustrated embodiment, an interior lumen 114 also extends between the proximal end and distal end 112 of the elongate tube 110.

The diffuser 120 may be coupled to the elongate tube 110 adjacent the distal end 112 of the elongate tube 110. In the illustrated embodiment, the diffuser 120 comprises an upper surface 122 and a lower surface 124. The upper 122 and lower 124 surfaces may each be coupled to support structures 125. The support structures 125 may be disposed such that they displace the upper 122 and lower 124 surfaces apart from each other, creating an open interior portion 128 between the two surfaces 122, 124. Support structures 125 may comprise walls, columns, cross-members, connection points, or other structures configured to offset the upper 122 and lower 124 surfaces while also coupling the upper 122 and lower 124 surfaces to each other. The interior portion 128 may be in fluid communication with the exterior environment at the outer edge of the diffuser 120 though openings 129 at the edge of the interior portion 128.

In the illustrated embodiment, the elongate tube 110 is coupled to the upper surface 122 such that the lumen 114 is in fluid communication with the interior portion 128 of the diffuser 120. For example, the upper surface 122 may comprise a hole positioned such that the interior portion 128 of the diffuser 120 is in communication with the lumen 114, while the elongate tube 110 is coupled to the upper surface 122 such that the lumen 114 is not in direct fluid communication with the exterior environment. In other words, fluid flow through the lumen 114 may be forced through the interior portion 128 of the diffuser 120.

Figure 2:
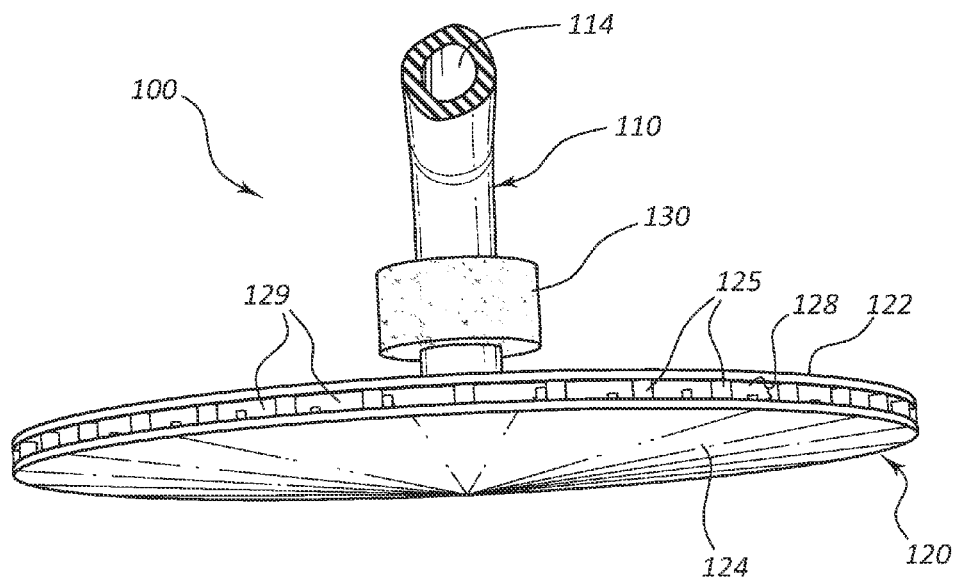
FIG. 2 is another perspective view of the catheter of FIG. 1.

FIG. 2 is another perspective view of the catheter of FIG. 1. Referring to both FIGS. 1 and 2, in the illustrated embodiment, the upper 122 and lower 124 surfaces may be configured to direct fluid flow through the catheter 100. For example, fluid flowing through the lumen 114 in a proximal to distal direction may pass from the lumen 114 to the interior portion 128 of the diffuser 120. The flow may then be directed by the upper 122 and lower 124 surfaces to the openings 129 at the outer edge of the diffuser 120. Similarly, in other instances, flow may enter the interior portion 128 of the diffuser 120 through the openings 129 at the outer edge of the diffuser 120 and flow into the lumen 114 in a distal to proximal direction.

FIGS. 1 and 2 further illustrate a cuff 130 coupled to the elongate tube 110. The cuff 130 may be configured to permit tissue ingrowth into the cuff 130, thus anchoring the catheter 100 while implanted in a patient's body. In some embodiments the cuff 130 may be comprised of a polymer such as Dacron. Additionally, FIGS. 1 and 2 also illustrate a bend 116 in the elongate tube 110. In some embodiments the elongate tube 110 may be configured with a bend 116 when the elongate tube 110 is unconstrained, in some instances to facilitate implantation or positioning within the body.

Figure 3:
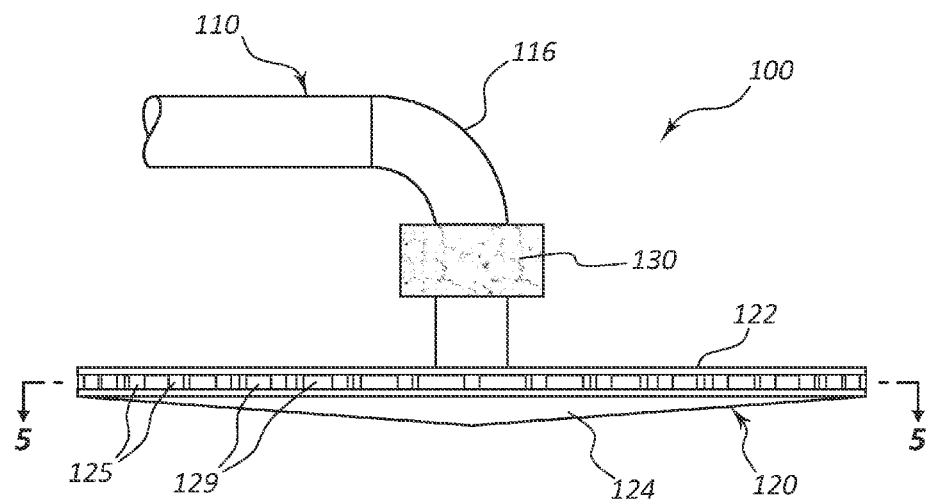
FIG. 3 is a side view of the catheter of FIG. 1.

FIG. 3 is a side view of the catheter of FIGS. 1 and 2. As show in FIGS. 2 and 3, the lower surface 124 of the diffuser may comprise a shallow conical shape in some embodiments. In some embodiments the support structures 125 thus may be somewhat thicker toward the center of the diffuser 120 than toward the edges, thus giving the lower surface a conical shape. This shape may be configured to reduce hydraulic resistance and provide greater flow area near the center of the diffuser 120. The conical shape may further be configured to facilitate rolling or folding the diffuser 120 around the elongate tube 110, as further discussed below.

Notwithstanding the shallow conical shape of the lower surface 124, FIG. 3 also illustrates how, in some embodiments, the upper 122 and lower 124 surfaces may be disposed substantially parallel. Further, in other embodiments, the upper surface 122 may also comprise a raised center point or other shape. In other embodiments both surfaces 122, 124 may be substantially flat.

Figure 4:
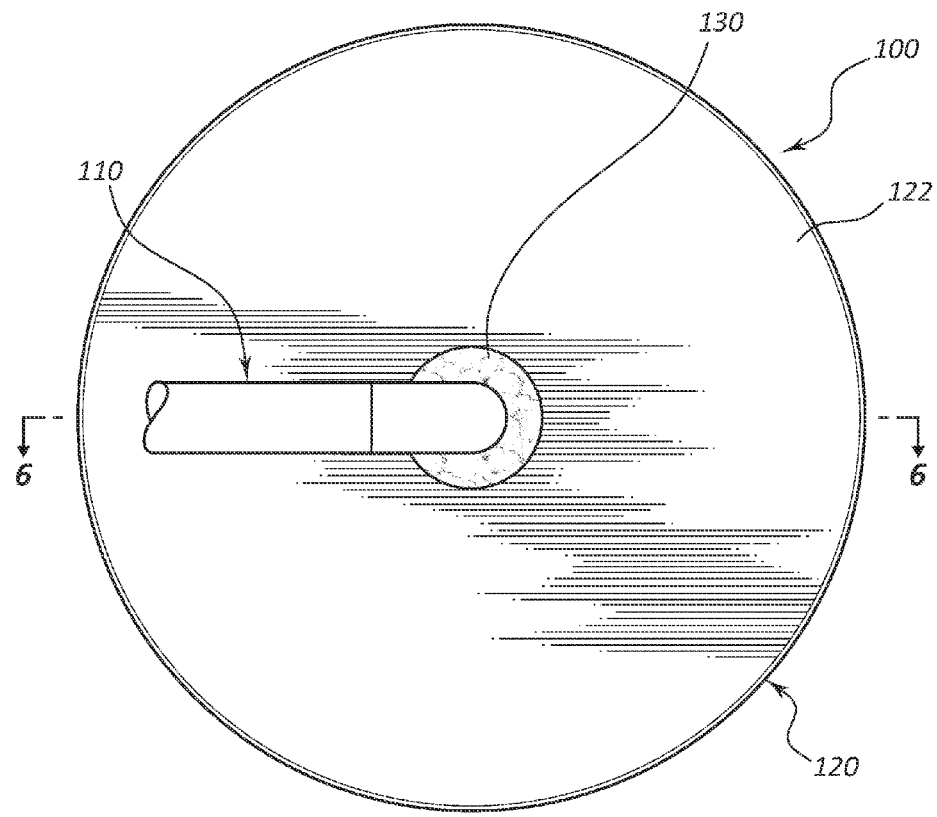
FIG. 4 is a top view of the catheter of FIG. 1.

FIG. 4 is a top view of the catheter of FIG. 1, showing the upper surface 124, the elongate tube 110, and the cuff 130. As shown in the illustrated embodiment, in some instances the upper surface 122 may comprise a generally circular profile. Similarly, the lower surface 124 (FIGS. 1-3) may comprise a generally circular profile having substantially the same diameter as the upper surface 122. Thus, the two surfaces, taken together, may create a substantially disc-shaped diffuser 120. In other embodiments the diffuser 120 may comprise other shapes, such as oval, square, rectangular, polygonal, and so forth.

Diffusers such as diffuser 120 of FIG. 4 may be configured to allow the catheter 100 to be configured with a relatively large number of small profile openings 129. For example, a single large opening may have a tendency to become blocked due to structures within a patient's body. Smaller openings may resist such blockage, though a larger number of openings may be needed to maintain a large flow path. Thus, diffusers may be configured to distribute flow and resist blockage of the openings.

In some embodiments the upper 122 and lower 124 surfaces may comprise a disc having a diameter from about 0.5 inch to about 4 inches, including diameters from about 0.75 inch to about 3 inches, or diameters of about 2.5 inches.

Figure 5:
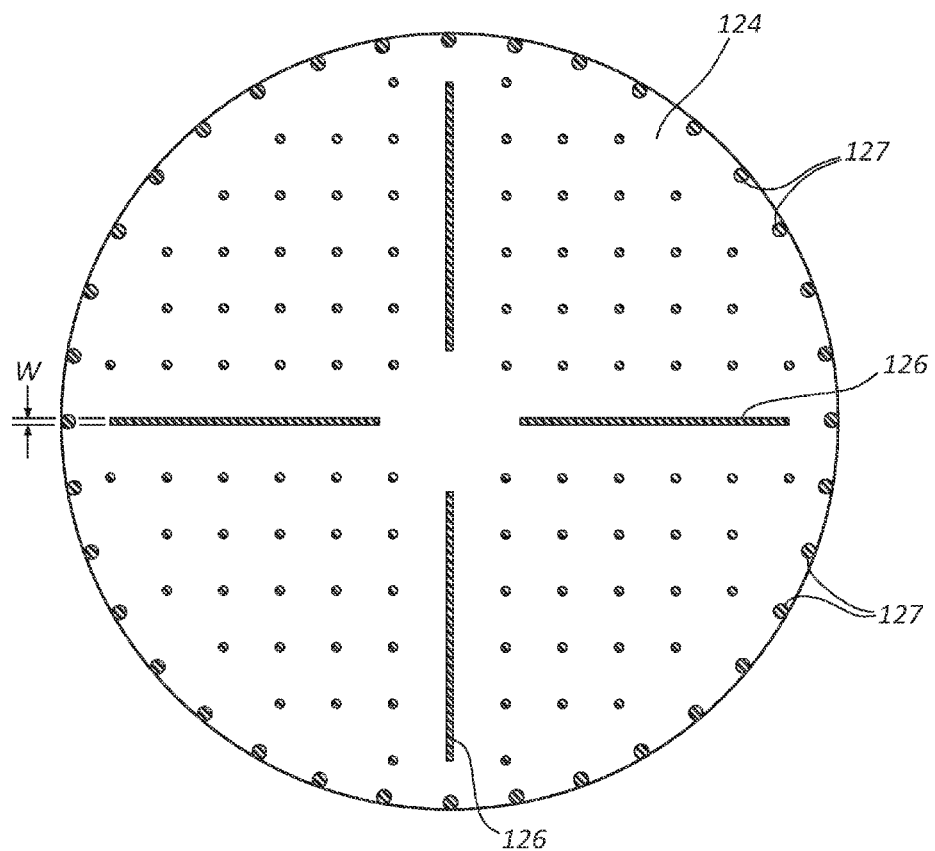
FIG. 5 is a cross-sectional view of the catheter of FIG. 3, taken through plane 5-5.

FIG. 5 is a cross-sectional view of the catheter of FIG. 3, taken through plane 5-5 shown in FIG. 3. FIG. 5 illustrates two types of support structures (125 of FIG. 3), walls 126 and connection points 127. In some embodiments the connection points may comprise points of adhesive disposed to couple the upper 122 and lower 124 surfaces. In other embodiments support structures may comprise also or alternatively comprise columns, or walls or connection points of shapes other than those shown.

As described above, the walls 126 and connection points 127 may be configured to both couple the upper 122 (FIGS. 1-4) and lower 124 surfaces to each other, and to create axial displacement between the upper 122 (FIGS. 1-4) and lower 124 surfaces. In other words, the height of the walls 126 of the thickness of the coupling material used at the connection points 127 may be configured to maintain a gap between the upper 122 (FIGS. 1-4) and lower 124 surfaces. In embodiments wherein adhesive is used at the connection points 127, the thickness of the adhesive may create such a gap. In embodiments where one or both surfaces comprise a conical shape, the walls 126 and/or connection points 127 may have varying heights to create the desired profile. The walls 126 and/or connection points 127 may be arranged or configured in a variety of ways. For example, in the illustrated embodiment connection points 127 are positioned at the outer edge of the lower surface 124. In other embodiments, the walls 126 may additionally or alternatively extend to the outer edge as well.

Figure 6:
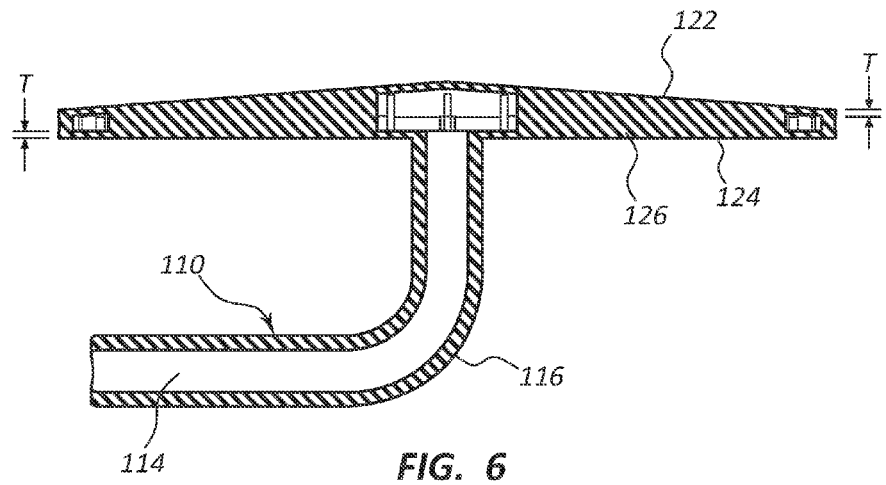
FIG. 6 is a cross-sectional view of the catheter of FIG. 4, taken through plane 6-6.

FIG. 6 is a cross-sectional view of the catheter of FIG. 4, taken through plane 6-6 of FIG. 4. As shown in FIG. 6, plane 6-6 intersects two walls 126 of the diffuser, as well as the elongate tube 110, the upper 122 and lower 124 surfaces, and connection points 127. (Note: The cuff 130 (FIGS. 1-4) is not shown in FIG. 6.) In the illustrated embodiment, the walls 126 and connection points 127 are taller near the center of the diffuser, thus creating and conforming to the shallow conical shape of the lower surface 124.

The upper 122 and lower 124 surfaces may be comprised of molded or sheet silicone in some embodiments, including sheets having a thickness from about 0.005 inch to about 0.040 inch, including from about 0.010 inch to about 0.040 inch, from about 0.015 inch to about 0.025 inch, or about 0.020 inch. In some embodiments the upper 122 and lower 124 sheets may not necessarily have the same thickness.

FIG. 6 also illustrates the lumen 114 disposed within the elongate tube 110. The lumen 114 may have a diameter from about 0.5 mm to about 5 mm, including from about 0.5 mm to about 3.5 mm, from about 0.5 mm to about 2.5 mm, or from about 0.5 mm to about 2 mm.

In some embodiments, the walls 126 may be formed of the same material as the upper 122 and lower 124 surfaces. For example, in embodiments where the surfaces 122, 124 are cut from sheets of material, the walls 126 may be cut from the same sheets. Thus, in some embodiments the width (W of FIG. 5) of the walls 126 may be the same as the thickness (T of FIG. 6) of the upper 122 and lower 124 surfaces.

Figure 7:
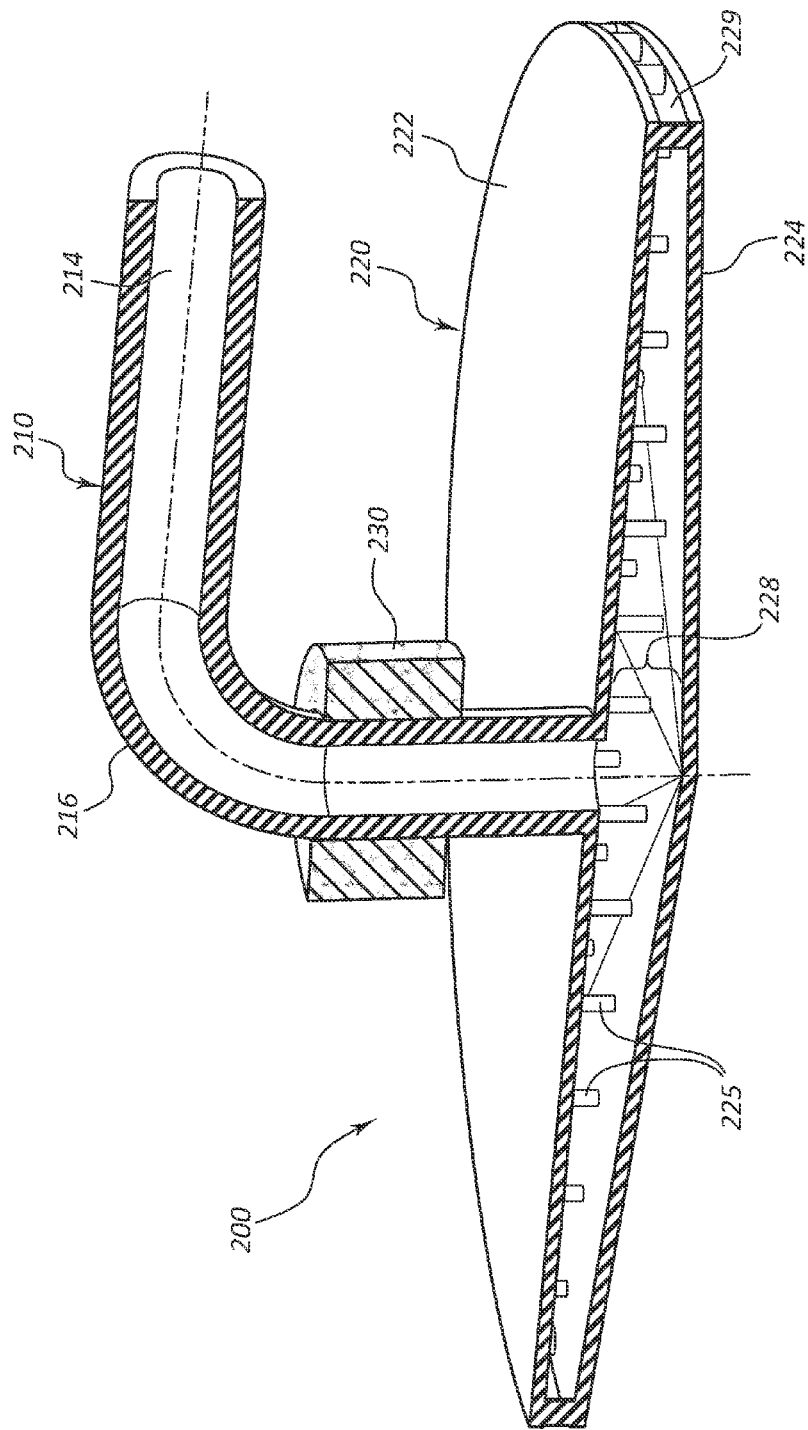
FIG. 7 is a cross-sectional perspective view of another embodiment of a catheter.

FIG. 7 is a cross-sectional view of another embodiment of a catheter 200 that can, in certain respects, resemble components of the catheter 100 described in connection with FIGS. 1-6 above. It will be appreciated that all the illustrated embodiments may have analogous features. Accordingly, like features are designated with like reference numerals, with the leading digits incremented to "2." (For instance, the catheter is designated "100" in FIG. 1, and an analogous catheter is designated as "200" in FIG. 7.) Relevant disclosure set forth above regarding similarly identified features thus may not be repeated hereafter. Moreover, specific features of the catheter and related components shown in FIG. 7 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the catheter of FIG. 7. Any suitable combination of the features, and variations of the same, described with respect to the catheter and components illustrated in FIGS. 1-6, can be employed with the catheter and components of FIG. 7, and vice versa. This pattern of disclosure applies equally to further embodiments depicted in subsequent figures and described hereafter.

The catheter 200 of FIG. 7 comprises an elongate tube 210 with an interior lumen 214 coupled to a diffuser 220. The diffuser 220 comprises an upper surface 222, a lower surface 224 and an interior portion 228 in fluid communication with the lumen 214. Support structures 225 are also shown between the upper 222 and lower 224 surfaces. The catheter 200 also comprises a cuff 230 and a bend 216 in the elongate tube 210.

FIG. 7 further illustrates the longitudinal axis of the elongate tube 210. As shown in FIG. 7, the longitudinal axis of the elongate tube 210 is an imaginary line along the center of the elongate tube 210. Thus, the longitudinal axis, as used to describe the catheters described herein, refers to a line along the center of the elongate tube—which line may or may not be straight. For example, because the elongate tube of FIG. 7 includes a bend 216, the longitudinal axis follows the bend 216.

In some embodiments, such as that illustrated in FIG. 7, the diffuser 220 may be oriented substantially perpendicular to the longitudinal axis of the elongate tube 210 when the catheter 200 is unconstrained.

Further, the bend 216 may be configured to facilitate use of the catheter 200 within the human body. In some embodiments, the bend 216 may comprise a substantially 90-degree angle. In other embodiments the bend 216 may form an acute angle in the elongate tube 210.

Figure 8A:
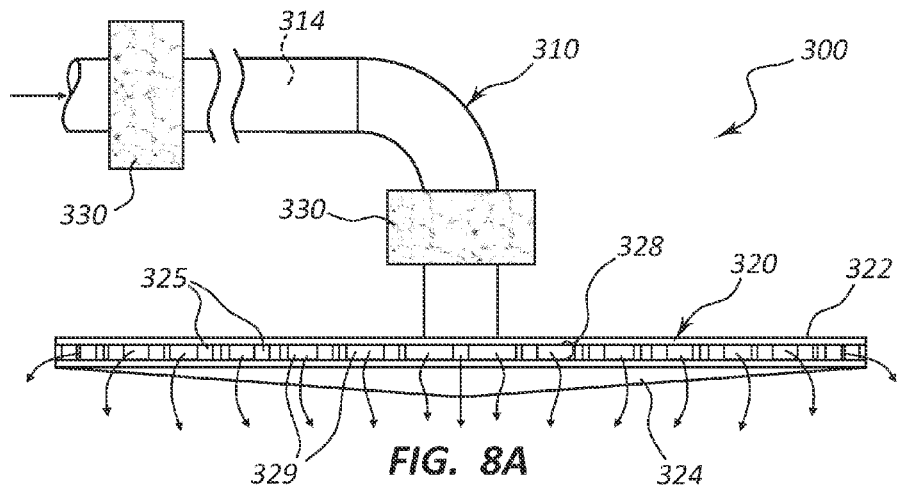
FIG. 8A is a side view of another embodiment of a catheter illustrating flow out of the catheter.
Figure 8B:
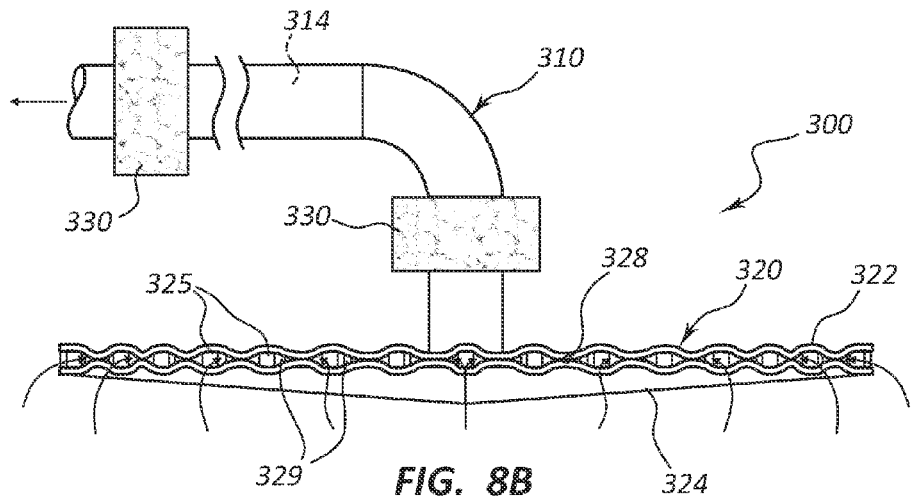
FIG. 8B is a side view of the catheter of FIG. 8A, illustrating flow into the catheter.

FIG. 8A is a side view of another embodiment of a catheter 300 illustrating flow out of the catheter 300. FIG. 8B is a side view of the catheter 300 of FIG. 8A, illustrating flow into the catheter 300. The catheter 300 of FIGS. 8A and 8B comprises an elongate tube 310 and a diffuser 320. Flow enters and exits the diffuser 320 at the outer edge of the diffuser 320, between the upper 322 and lower 324 surfaces of the diffuser 320. The catheter 300 further comprises two cuffs 330.

FIG. 8A illustrates how flow through the lumen 314 of the elongate tube 310 in a proximal to distal direction is directed through the interior portion 328 of the diffuser 320 and out of the edge of the diffuser 320. Similarly, FIG. 8B illustrates how flow may enter the diffuser 320 at the edge of the diffuser 320 and subsequently proceed through the lumen 314 in a distal to proximal direction.

In some instances, flow into the diffuser 320 from the outside environment results from negative pressure in the lumen 314 with respect to the outside environment. This creates negative pressure within the interior portion 328 of the diffuser 320 which may then draw flow into the diffuser 320. In some embodiments, the upper 322 and lower 324 surfaces may be comprised of flexible materials. In such instances, negative pressure within the interior portion 328 of the diffuser may tend to collapse the upper 322 and lower 324 surfaces into the interior portion 328, as shown in FIG. 8B.

Support structures 325 such as walls or connection points disposed near the outer edge of the diffuser 320 may prevent the surfaces 322, 324 from completely collapsing and closing off flow into the diffuser 320. For instance, in the embodiment of FIG. 8B, negative pressure collapsed the surfaces 322, 324 such that the openings 329 at the outer edge of the diffuser 320 form substantially triangular shapes. Thus, in some embodiments, support structures 325 disposed near the outer edge of the diffuser 320 may be configured to prevent collapse of the openings 329 in the diffuser 320. Additionally, the relative size of the openings 329 may decrease as the surfaces 322, 324 collapse under negative pressure. In some embodiments, the surfaces 322, 324 may be configured as sufficiently flexible to collapse and reduce the size of the openings 329 in order to further limit the tendency of the omentum or other structures from occluding the openings 329.

Figure 8C:
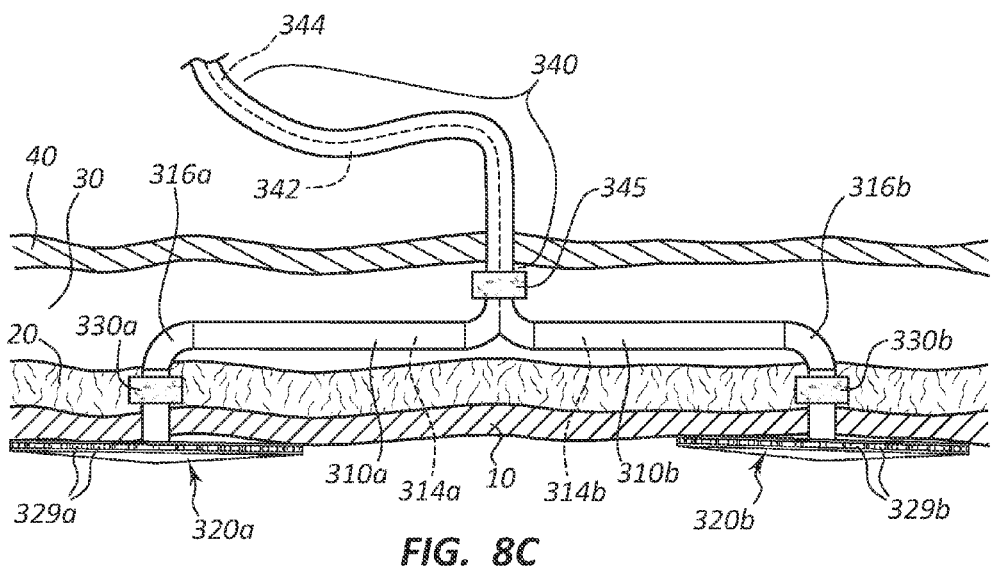
FIG. 8C is a side view of a catheter assembly in use within a patient.

FIG. 8C is a side view of a catheter assembly in use within a patient. The catheter assembly shown comprises a first elongate tube 310a coupled to a first diffuser 320a and a second elongate tube 310b coupled to a second diffuser 320b. A cuff 330a, 330b is associated with each elongate tube 310a, 310b and diffuser 320a, 320b. Further, each elongate tube 310a, 310b comprises an interior lumen 314a, 314b. The elongate tubes 310a, 310b are coupled to a proximal catheter portion 340 adjacent the proximal end of each tube 310a, 310b. The proximal catheter portion 340 may comprise two interior lumens 342, 344, each in fluid communication with one of the interior lumens 314a, 314b of the elongate tubes 310a, 310b. That is, interior lumen 342 may be in fluid communication with the interior lumen 314a and interior lumen 344 may be in fluid communication with interior lumen 314b. In some embodiments the two lumens of the proximal catheter portion 340 may be arranged in a double-D profile. Finally, a proximal cuff 345 may be coupled to the proximal catheter portion 340.

A catheter assembly such as that shown in FIG. 8C may be configured to provide flow across the abdominal wall, for example for use in connection with peritoneal dialysis. More particularly, the assembly of FIG. 8C may be configured to provide unidirectional flow through the peritoneal space, including flow out of one diffuser (e.g. 320a) and out of a second diffuser (e.g. 320b).

In some embodiments, peritoneal dialysis may be performed in connection with a single elongate tube 310a, 310b and a single diffuser 320a, 320b. For instance, a catheter assembly may be configured with an elongate tube, a diffuser, and a proximal catheter portion having only one lumen. For convenience, the reference numerals associated with the first elongate tube 310a and the first diffuser 320a will be used to describe an exemplary procedure using a catheter with only one elongate tube and lumen.

The catheter assembly may be disposed within the body such that the proximal catheter portion 340 and the elongate tube 310a cross abdominal wall 10 of a patient, facilitating flow in and out of the patient's body. The diffuser 320a may be positioned against the abdominal wall 10 such that flow out of the diffuser 320a is directed along the inside of the abdominal wall 10. A practitioner may utilize such an assembly to infuse or introduce dialysis fluid into a patient. After a sufficient amount of fluid is introduced, and toxins allowed to diffuse into the fluid, the dialysis fluid may then be drained from the patient. The same catheter assembly may be utilized to drain the fluid, by introducing flow through the assembly in the opposite direction.

The diffuser 320a may be configured to limit the extent to which bodily structures interfere with flow out of the body. For example, the position of the diffuser next to the abdominal wall, the relatively thin profile of openings (329 in FIGS. 8A and 8B), and the distribution of the openings along the outer edge of the diffuser 320a may each affect the tendency of bodily structures to impede flow into the diffuser 320a. For example, during peritoneal dialysis, the omentum may tend to block flow into the diffuser 320a. The features described above may limit the extent to which the omentum blocks the flow. For example, the omentum may be too thick or stiff to clog the small profile openings (329 in FIGS. 8A and 8B) in the diffuser 320a. Catheters configured to resist such blockage may thus have higher flow rates and longer effective use periods than other catheters. Additionally, the diffuser 320a may be configured to inhibit or prevent the catheter assembly from moving outward from the wall of the rectus muscle 20.

The cuff 330a may be positioned within the rectus muscle 20 when the catheter assembly is implanted in a patient. Tissue ingrowth into the cuff 330a may anchor the assembly and prevent accidental movement or removal of the assembly. Furthermore the proximal cuff 345 may be positioned in the subcutaneous fat tissue 30, again anchoring the assembly. The proximal catheter portion 340 may emerge through a single opening in the skin 40 of the patient.

In some instances, catheters utilizing diffusers such as those disclosed herein may be configured to provide high flow rates through the catheter. For example, in some instances flow rates of 100-200 ml/min may be obtained in connection with the catheters disclosed herein. High flow rates may correlate with shorter fluid exchange times for dialysis patients. Further, high flow rates may also tend to more completely drain dialysis fluid than catheters with more hydraulic resistance. For example, in some embodiments the catheters disclosed herein may have ⅓ the hydraulic resistance of other catheters, such as the Tenkhoff dialysis catheter.

A catheter assembly comprising two diffusers 320a, 320b (i.e., the entire assembly of FIG. 8C) may be configured for "continuous flow" peritoneal dialysis. In other words, the system may be configured with a diffuser providing flow out of the diffuser, such as diffuser 320a, and a diffuser simultaneously providing flow into the diffuser, such as diffuser 320b. In other words, one diffuser 320a may infuse dialysis fluid into a patient while the other diffuser 320b simultaneously withdraws fluid from the body. The components may be positioned and anchored as described in connection with the exemplary procedure which utilized a single diffuser. Additionally, in some instances, the diffuser providing flow out of the diffuser may be positioned higher in the abdominal wall of the patient than the diffuser providing flow into the diffuser, and the two diffusers offset transversely across the body. The diffusers may be arranged in different dispositions depending on the desired flow characteristics of the dialysis fluid.

FIG. 8C further illustrates how bends 316a, 316b may be configured to conform to the anatomy of a patient and facilitate implantation of the assembly.

FIG. 9A is a side view of a catheter 400a within a delivery lumen 450a. As described above, the diffuser 420a may be comprised of flexible materials to facilitate introduction of the diffuser 420a into the body. Specifically, diffusers 420a comprised of flexible components may be rolled, folded, or otherwise constrained within a delivery lumen 450a for introduction into the body. Once the diffuser 420a is deployed within the body the diffuser 420a may be configured to resume an open shape. Thus, in some embodiments the catheter may have a deployed configuration with a transverse coupled diffuser and one or more bends in the elongate tube (such as that shown in FIG. 8A) and a delivery or removal configuration where the diffuser and elongate tube are constrained within a delivery lumen 450a. In some instances the diffuser 420a may be constrained such that it lies adjacent the longitudinal axis of the elongate tube 410a. In the embodiment of FIG. 9A, the diffuser 420a is simply folded up, analogous to an umbrella, within the delivery lumen 450a.

FIG. 9B is a side view of another embodiment of a catheter 400b within a lumen 450b. Flexible diffusers may also be configured to facilitate removal from the body. For instance, a diffuser may be removed from the body through a lumen 450b. In some embodiments the diffuser 420b is pulled into the lumen 450b, causing the diffuser 420b to fold up in a reverse umbrella type configuration. In embodiments utilizing cuffs (such as that of FIG. 8C) the cuffs may be dislodged from the body prior to removal of the diffuser. Furthermore, in some embodiments the diffuser 420b may simply be pulled through the opening in the body, with the body constraining the diffuser 420b into a reverse umbrella shape rather than a lumen 450b.

Figure 10:
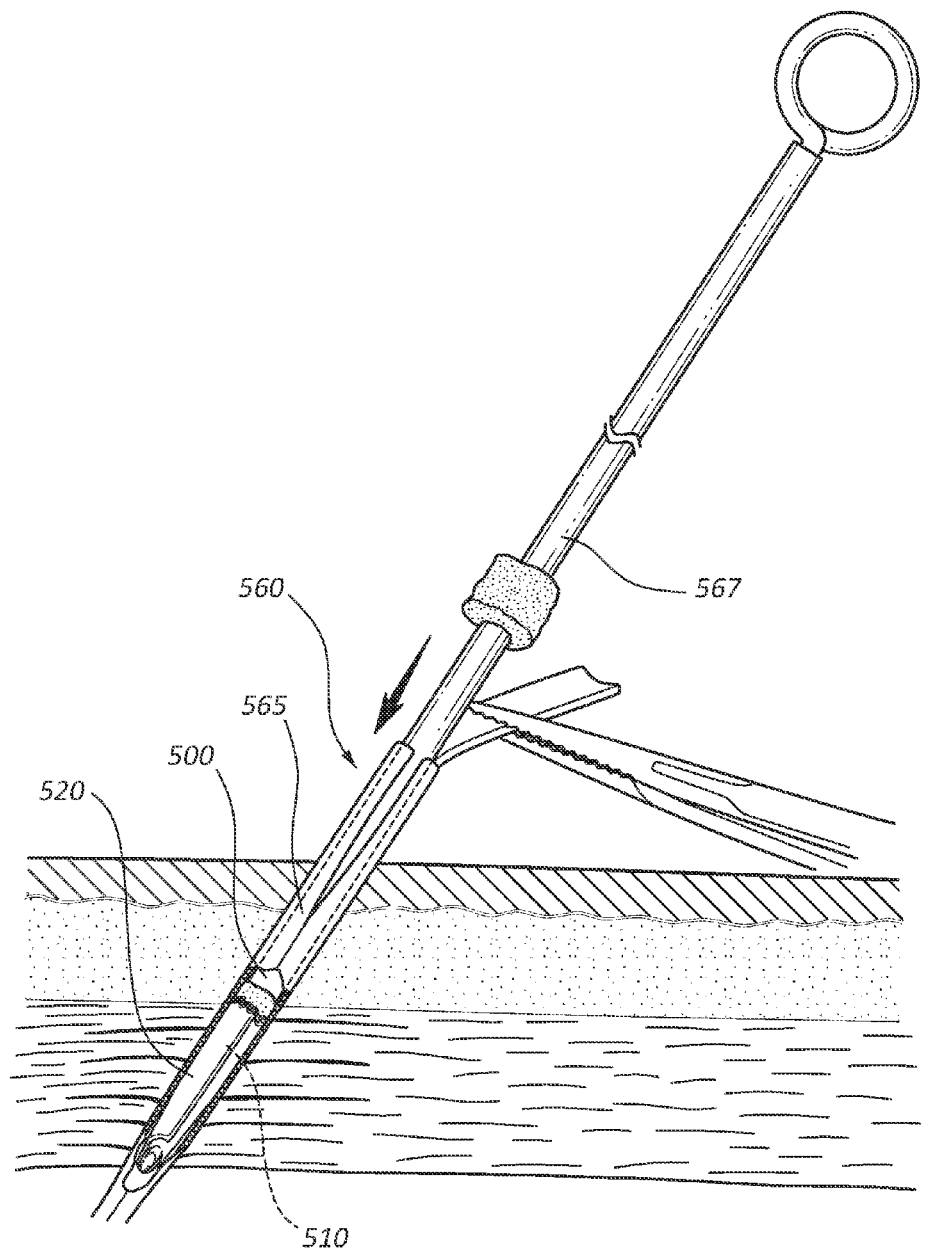
FIG. 10 is a side view of a catheter within a delivery device during insertion in a patient.

FIG. 10 is a side view of a catheter 500 within a delivery device 560. In some embodiments, the diffuser 520 may be rolled around the elongate tube 510 of the catheter 500 when the catheter 500 is disposed in a delivery or constrained configuration. Further, split sheath introducers such as the Quill Guide® may be utilized to insert the catheter 500 into the body. For example, a needle or trocar may be used to create a small opening in the body and the split sheath guide 565 and catheter 500 inserted through the opening. A stylet 567 or other instrument may be used to advance the catheter 500 and/or split sheath guide 565 through the opening into the desired position within the body. The split sheath guide 565 and stylet 567 may be removed, and the catheter 500 may assume a deployed configuration, for example with the diffuser 520 oriented perpendicular to the elongate tube 510.

Without further elaboration, it is believed that one skilled in the art can use the preceding description to utilize the present disclosure to its fullest extent. The examples and embodiments disclosed herein are to be construed as merely illustrative and exemplary and not as a limitation of the scope of the present disclosure in any way. It will be apparent to those having skill in the art, and having the benefit of this disclosure, that changes may be made to the details of the above-described embodiments without departing from the underlying principles of the disclosure herein.

The invention claimed is:

1. A catheter comprising:
   an elongate lumen extending between a proximal end and a distal end, and
   a diffuser coupled to the distal end of the lumen, the diffuser comprising:
      a flexible upper surface extending radially from the distal end of the lumen when the catheter is in a deployed configuration,
      a flexible lower surface, wherein the lower surface forms a conical shape,
      an interior portion disposed between the upper and lower surfaces, and
      a plurality of walls disposed between and coupled to the upper and lower surfaces, wherein the walls are thicker adjacent a center of the diffuser in relation to the thickness of the walls adjacent a circumference of the diffuser, such that the walls conform to the conical shape of the lower surface,
   wherein the interior portion is in fluid communication with the lumen.

2. The catheter of claim 1, wherein the diffuser comprises a disc.

3. The catheter of claim 2, wherein the disc is from about 0.05 inch to about 4 inches in diameter.

4. The catheter of claim 1, wherein the upper surface is configured to be disposed adjacent a circumference of a distal portion of the lumen when the catheter is in a delivery configuration.

5. The catheter of claim 4, wherein the diffuser is configured to return to the deployed configuration when not constrained.

6. The catheter of claim 1, wherein the plurality of walls are from about 0.010 inch to about 0.040 inch high.

7. The catheter of claim 1, further comprising a plurality of connection points, wherein the upper and lower surfaces are coupled to each other at the connection points.

8. The catheter of claim 7, wherein the upper and lower surfaces are coupled at the connection points by an adhesive.

9. The catheter of claim 7, wherein one or more connection points are disposed adjacent a circumference of the diffuser.

10. The catheter of claim 7, wherein one or more walls extend to a circumference of the diffuser.

11. The catheter of claim 1, further comprising a plurality of openings adjacent the circumference of the diffuser.

12. The catheter of claim 11, wherein the openings are disposed between connection points or walls disposed adjacent the circumference of the diffuser.

13. The catheter of claim 12, wherein the openings partially collapse to form triangular shapes when fluid pressure in the interior portion is lower than fluid pressure outside the diffuser.

14. The catheter of claim 1, wherein the lumen forms a bend between the proximal and distal ends of the lumen when the lumen is unconstrained.

15. The catheter of claim 1, further comprising a first cuff coupled to the lumen, the first cuff configured to permit tissue ingrowth into the first cuff.

16. The catheter of claim 15, further comprising a second cuff, wherein the first cuff is configured to be disposed in the subcutaneous fat tissue and the second cuff is configured to be disposed in the rectus muscle.

17. The catheter of claim 1, further comprising:
- a second elongate lumen extending between a proximal end and a distal end,
- a second diffuser coupled to the distal end of the second lumen, the second diffuser comprising:
- a second flexible upper surface extending radially from the distal end of the second lumen when the catheter is in a deployed configuration,
- a second flexible lower surface, and
- a second interior portion disposed between the second upper and lower surfaces;
- wherein the second interior portion is in fluid communication with the second lumen; and
- a proximal catheter portion coupled to the proximal end of the lumen and the second lumen, and having a third lumen and a fourth lumen, the third lumen in fluid communication with the lumen and the fourth lumen in fluid communication with the second lumen.

* * * * *